(12) United States Patent
Doherty et al.

(10) Patent No.: US 10,568,856 B2
(45) Date of Patent: Feb. 25, 2020

(54) COMPOSITION FOR IMPROVED SLEEP

(71) Applicant: Jamieson Laboratories, Ltd., Toronto (CA)

(72) Inventors: John Doherty, Windsor (CA); Soring Popa, Windsor (CA); Dore Miller, Windsor (CA); Marc Bellemore, Windsor (CA)

( * ) Notice: Subject to any disclaimer, the term of this patent is extended or adjusted under 35 U.S.C. 154(b) by 70 days.

(21) Appl. No.: 15/755,349

(22) PCT Filed: Aug. 31, 2016

(86) PCT No.: PCT/CA2016/000222
§ 371 (c)(1),
(2) Date: Apr. 16, 2018

(87) PCT Pub. No.: WO2017/035631
PCT Pub. Date: Mar. 9, 2017

(65) Prior Publication Data
US 2019/0240178 A1 Aug. 8, 2019

Related U.S. Application Data

(60) Provisional application No. 62/212,627, filed on Sep. 1, 2015.

(51) Int. Cl.
| | | |
|---|---|---|
| *A61K 31/19* | (2006.01) | |
| *A61K 9/24* | (2006.01) | |
| *A61P 25/20* | (2006.01) | |
| *A61K 31/198* | (2006.01) | |
| *A61K 31/4045* | (2006.01) | |
| *A61K 36/28* | (2006.01) | |
| *A61K 36/41* | (2006.01) | |
| *A61K 36/539* | (2006.01) | |
| *C07C 229/24* | (2006.01) | |
| *A61K 9/00* | (2006.01) | |
| *A61K 45/06* | (2006.01) | |
| *C07D 209/14* | (2006.01) | |

(52) U.S. Cl.
CPC ............. *A61K 31/198* (2013.01); *A61K 9/00* (2013.01); *A61K 9/209* (2013.01); *A61K 31/4045* (2013.01); *A61K 36/28* (2013.01); *A61K 36/41* (2013.01); *A61K 36/539* (2013.01); *A61K 45/06* (2013.01); *A61P 25/20* (2018.01); *C07C 229/24* (2013.01); *C07D 209/14* (2013.01); *A61K 2300/00* (2013.01)

(58) Field of Classification Search
CPC .... A61K 31/198; A61K 31/4045; A61K 9/00; A61K 9/209; A61K 2300/00; A61P 25/20
See application file for complete search history.

(56) References Cited

U.S. PATENT DOCUMENTS

2009/0175936 A1* 7/2009 Rohr .................... A61K 9/2072
424/464

FOREIGN PATENT DOCUMENTS

| WO | 2012116445 | 9/2012 |
| WO | 2013113027 | 8/2013 |
| WO | 2014186410 | 11/2014 |

OTHER PUBLICATIONS

PCT/CA2016/000222 Written Opinion, dated Oct. 24, 2016.

* cited by examiner

*Primary Examiner* — Zohreh A Fay

(57) ABSTRACT

Compositions are disclosed for improved sleep quality and quantity including ingredients for both immediate release and controlled release. The invention provides improved supplemental compositions, and methods for administering same to a user, for enhancing the onset, quality, and duration of sleep in humans and animals. The supplemental composition may contain a combination of ingredients in proportions calculated to relieve stress, promote relaxation, and enhance sleep, including at least the following ingredients: L-Theanine, Skullcap Herb (*Scutellaria lateriflora* L.), Rhodiola (*Rhodiola rosea* L.), and Chamomile Flower (*Matricaria Recutita*). In addition, the supplemental composition may include the secondary ingredient Melatonin. The selection and amounts of the ingredients of the supplemental composition promote sleep onset, quality, and duration and may be provided for consumption at least one time daily, e.g., prior to sleep. The composition may be in a layered solid dosage form to provide controlled and sustained release of specific ingredients.

5 Claims, No Drawings

COMPOSITION FOR IMPROVED SLEEP

RELATED APPLICATIONS

This application is a national filing claiming priority from PCT application number PCT/CA2016/000222, filed on Aug. 31, 2016, which is an international filing under the Patent Cooperation Treaty claiming priority from U.S. provisional patent application Ser. No. 62/212,627, filed on Sep. 1, 2015.

FIELD OF THE INVENTION

The present invention pertains to the field of dietary supplements. More particularly, the invention pertains to the use of a specific supplementary composition as an aid in the induction and maintenance of sleep in a user, e.g., human. The invention also pertains to the use of a specific supplementary composition as a calmative, sedative, adaptogen to relieve stress, and aid in cognitive function.

BACKGROUND OF THE INVENTION

Sleep can be defined as an active, repetitive, and reversible state of perceptual disengagement from and unresponsiveness to the environment. Empirical evidence demonstrates an association between sleep and the consolidation of cognitive performance, which is required for executive functioning including abstract reasoning, goal directed behavior, and creative processing. (Carskadon M A, et al. (2005). Normal human sleep: an overview. In: Kryger M H, et al. eds. *Principle and practice of sleep medicine*. 4th ed. Philadelphia: Elsevier Saunders; p. 13-23; Walker M P, et al. (2002). Cognitive flexibility across the sleep wake cycle: REM-sleep enhancement of anagram problem solving. *Brain Res Cogn Brain Res* 2002; 14: 317-324; Curcio G, et al. (2006). Sleep loss, learning capacity, and academic performance. *Sleep Med Rev*, 10: 323-327.)

The sleep-related overnight brain processes are thought to influence cognitive, physical and emotional performance throughout the day due to impairment of the executive function of the prefrontal cortex. Shortness or disruption of sleep reduces necessary overnight brain activity that is needed for higher order neurocognitive functioning, and results in a decline in the ability to complete complex tasks requiring abstract thinking, creativity, integration, and planning. (Dewald J F, et al. (2010). The influence of sleep quality, sleep duration, and sleepiness on school performance in children and adolescents: A meta-analytic review. *Sleep Med Rev*, 14: 179-189; Dahl R E. (1996). The regulation of sleep and arousal: development and psychopathology. *Dev Psychopathol* 8: 3-27; Harrison Y, et al. (1998). Sleep loss impairs short and novel language tasks having a prefrontal focus. *J Sleep Res*, 7: 95-100.)

Sleep is clinically important for a variety of reasons. Firstly, complaints about sleep quality are common; epidemiological surveys indicate that 15-35% of the adult population complain of impaired sleep quality, such as difficulty in inducing or maintaining sleep. (Buysse D J, et al. (1988). The Pittsburgh Sleep Quality Index: A New Instrument for Psychiatric Practice and Research. *Psychiatry Res*, 28(2): 193-213; Karacan I, et al. (1976). Prevalence of sleep disturbances in a primarily urban Florida county. *Soc Sci Med*, 10: 239-244; Karacan I, et al. (1983). Sleep disturbance: A community survey. *Sleep/Wake Disorders: Natural History, Epidemiology, and Long-Term Evolution*. New York: Raven Press, 1983. pp. 37-60; Bixler E O, et al. (1979). Prevalence of sleep disorders in the Los Angeles Metropolitan area. *Am J Psychiatry*, 136: 1257-1262; Lugaresi E, et al. (1983). Good and poor sleepers: An epidemiological survey of the San Marion population. In: Guilleminault, C., and Lugaresi, E., eds. *Sleep/Wake Disorders: Natural History, Epidemiology, and Long-Term Evolution*. New York: Raven Press, 1983. pp. 1-12. Welstein L., et al. (1983). Insomnia in the San Francisco Bay Area: A telephone survey. *Sleep/Wake Disorders: Natural History, Epidemiology, and Long-Term Evolution*. New York: Raven Press, 1983. pp. 73-85; Mellinger G D, et al. (1985). Insomnia and its treatment: Prevalence and correlates. *Archives Gen. Psychiatry*, 42: 225-232.)

In studies conducted on rats, sustained sleep deprivation caused severe weight loss, malnutrition, and death. (Everson C A. (1993). Sustained sleep deprivation impairs host defense. *Am J Physiol*, 265(5 Pt 2): R1148-1154.) Impaired sleep onset, quality, and duration have been shown to have significant impacts on cognitive and behavioural functioning in adults. In adults, sustained sleep deprivation results in poor modulation of immunity, a reduction in natural immune responses and T cell cytokine production, and an adverse effect on host resistance to infectious disease. (Irwin M, et al. (1996). Partial night sleep deprivation reduces natural killer and cellular immune responses in humans. FASEB J. 10(5): 643-653.) Significant associations have also been observed between impaired sleep and hypertension (Bansil P, et al. (2011). Associations Between Sleep Disorders, Sleep Duration, Quality of Sleep, and Hypertension: Results From the National Health and Nutrition Examination Survey, 2005 to 2008. *J. Clin Hypertens*, 13(10): 739-743.), incidence of coronary heart disease and cardiovascular disease (Hoevenaar-Blom M P, et al. (2011). Sleep Duration and Sleep Quality in Relation to 12-Year Cardiovascular Disease Incidence: The MORGEN Study. *Sleep*, 34(11): 1487-1492.), and increased risk of diabetes (Knutson K L, et al. (2006). Role of Sleep Duration and Quality in the Risk and Severity of Type 2 Diabetes Mellitus. *Arch Intern Med*, 166(16): 1768-1774.).

Additionally, sleep is crucial for children and adolescents' learning, memory processes and school performance. Insufficient sleep, poor sleep quality and sleepiness are common problems in children and adolescents, with reported prevalence varying from 11% to 47%. These problems seriously affect learning capacity, school performance, and neurobehavioural functioning. (Russo P M, et al. (2007). Sleep habits and circadian preference in Italian children and adolescents. *J Sleep Res*, 16: 163-169; Liu X, et al. (2002). Sleep duration, insomnia and behavioral problems among Chinese adolescents. *Psychiatry Res*, 111: 75-85. Dewald J F, et al. (2010). The influence of sleep quality, sleep duration, and sleepiness on school performance in children and adolescents: A meta-analytic review. *Sleep Med Rev*, 14: 179-189; Curcio G, et al. (2006). Sleep loss, learning capacity and academic performance. *Sleep Med Rev*, 10: 323-337; Fallone G, et al. (2002). Sleepiness in children and adolescents: clinical implications. *Sleep Med Rev*, 6: 287-306; Wolfson A R, et al. (2003). Understanding adolescents' sleep patterns and school performance: a critical appraisal. *Sleep Med Rev*, 7: 491-506.)

Gamma Aminobutyric Acid (GABA) is a primary inhibitory neurotransmitter of the central nervous system (CNS). It is well established that activation of GABA receptors favors the onset of sleep. The GABA-receptors are associated with chloride ion channels—signalling through the GABA-receptor changes the electrochemical gradient of the neutron, leading to activity inhibition (Olsen R W, Tobin A J. (1990). Molecular biology of GABAA receptors. *FASEB J.*, 4(5): 1469-1480).

Three generations of hypnotics are based on these GABAA receptor-mediated inhibitory processes, including barbiturates, benzodiazepines, imiddazyropyridines, and cyclopyrrolones. These hypnotics decrease waking, increase slow-wave sleep and enhance the intermediate stage situated between slow-wave sleep and paradoxical sleep. (Gottesmann C. (2002). GABA mechanisms and sleep. *Neuroscience*, 111(2): 231-239.) For example, benzodiazepines are thought to act via interaction with the GABA receptor; enhancing the inhibitory effects of GABA. As such, Benzodiazepines are a widely used class of drugs primarily used as tranquilizers, muscle-relaxants, hypnotics, or sedatives (Valenstein M, et al. (2004). Benzodiazepine use among depressed patients treated in mental health settings. *Am J Psychiatry*, 161(4): 654-661). Many of these classes of drugs, however, have been found to lead to dependence and other side effects. (Rao T P, et al. (2015). In search of a safe natural sleep aid. *J Am Coll Nutr*, 11: 1-12.)

L-Theanine, (γ-glutamylethylamide), an amino acid naturally found abundant in tea leaves, has anxiolytic effects via the induction of a brain waves without the side effects associated with conventional sleep inducers, and has achieved significant improvements in sleep quality and efficiency relative to placebo treatments in both pediatric and adult populations, with no significant adverse effects. (Rao T P, et al. (2015). In search of a safe natural sleep aid. *J Am Coll Nutr*, 11: 1-12; Barrett J R, et al. (2013). To sleep or not to sleep: A systematic review of the literature of pharmacological treatments of insomnia in children and adolescents with attention-deficit/hyperactivity disorder. *J Child Adol Psychop*, 23.10: 640-647; Jang H S, et al. (2012). L-theanine partially counteracts caffeine-induced sleep disturbances in rats. *Pharmacy Biochem Be*, 101(2): 217-221; Lyon M R, et al. (2011). The effects of l-theanine (Suntheanine®) on objective sleep quality in boys with attention deficit hyperactivity disorder (ADHD): a randomized, double-blind, placebo-controlled clinical trial. *Altern Med Rev*, 16(4): 348-354.)

Similarly, the side effects, tolerance, and dependency associated with benzodiazepines have led to studies of the use of *Scutellaria lateriflora*, or American Skullcap, to achieve anxiolytic effects. (del Mundo W F, Shepherd W C, Marose T D. 2002. Use of alternative medicine by patients in a rural family practice clinic. *Fam Med*, 34: 206-212; B.N.F. 2008. *British National Formulary* 55. BMJ Publishing Group and the RPS Publishing: London; Wolfson P, Hoffmann D L. 2003. An investigation into the efficacy of *Scutellaria lateriflora* in healthy volunteers. *Altern Ther Health Med*, 9: 74-78). Studies suggest that *Scutellaria lateriflora* may play a role in anxiolytic activity since its compounds are known to bind to the benzodiazepine site of the GABAA receptor (Awad R., et al. (2003). Phytochemical and biological analysis of Skullcap (*Scutellaria lateriflora* L.): A medicinal plant with anxiolytic properties. *Phytomedicine*, 10: 640-649.)

Additional studies have been conducted on the use of *Rhodiola rosea* L. (Rhodiola), a popular adaptogen in European and Asiatic traditional medicine. (German C, et al. (1999). Artic Root (*Rhodiola rosea*): the powerful ginseng alternative. Kensington Publishing Corp., New York; Spasov A A, et al. (2000). A double-blind, placebo-controlled pilot study of the stimulating and adaptogenic effect of *Rhodiola rosea* SHR-5 extract on the fatigue of students caused by stress during an examination period with a repeated low-dose regimen. *Phytomedicine*, 7(2): 85-89; Shevtsov V A, et al. (2003). A randomized trial of two different doses of a SHR-5 *Rhodiola rosea* extract versus placebo and control of capacity for mental work. *Phytomedicine*, 10(2-3): 95-105, Panossian A, Wagner H. (2005). Stimulating effect of adaptogens: an overview with particular reference to their efficacy following single dose administration. *Phytother Res* 19: 819-838). These studies have demonstrated pharmacological properties which include significant improvements in insomnia relative to placebo treatments without serious side effects (Darbinyan V, et al. (2007). Clinical trial of *Rhodiola rosea* L. extract SHR-5 in the treatment of mild to moderate depression. *Nord J Psychiatry*, 61: 343-348; Brown R P, Gerbarg P L, Ramazanov Z. 2002. *Rhodiola rosea*: a phytomedicinal overview. HerbalGram 56: 40-52.) *R. rosea* also possesses antistress properties due to its ability to modulate the activation of several components of the stress-response systems, such as the sympatho-adrenal system (Lishmanov Iu B, et al. (1987). Plasma beta-endorphin and stress hormones in stress and adaptation. *Biull Eksp Biol Med* 103(4): 422-424; Panossian A, et al. (1999). Plant adaptogens III. Earlier and more recent aspects and concepts on their mode of actions. *Phytomedicine*, 6: 287-300; Panossian A, Wagner H. (2005). Stimulating effect of adaptogens: an overview with particular reference to their efficacy following single dose administration. *Phytother Res* 19: 819-838) and the hypothalamic-pituitary-adrenal axis (Burchfield S R. (1979). The stress response: a new perspective. *Psychosom Med* 41(8): 661-672; Lishmanov I B, et al. (1987). Plasma beta-endorphin and stress hormones in stress and adaptation. *Biull Eksp Biol Med*, 103(4): 422-424; Saratikov A S, Krasnov E A (1987) *Rhodiola rosea* is a valuable medicinal plant (Golden Root). Tomsk State University Press, Russia; Panossian A, et al. (1999). Plant adaptogens III. Earlier and more recent aspects and concepts on their mode of actions. *Phytomedicine*, 6: 287-300; Panossian A, Wagner H. (2005). Stimulating effect of adaptogens: an overview with particular reference to their efficacy following single dose administration. *Phytother Res* 19: 819-838). Furthermore, *R. rosea* possesses the ability to reduce the secretion of corticotrophin-releasing factor (CRF), the major physiological mediator of stress (Lishmanov, maslova) which may have significant impacts on the reduction of insomnia and the overall improvement of sleep onset, quality, and duration.

Studies conducted on the use of *Matricaria ricutita* (chamomile), which also binds to GABA receptors and has been found to have benzodiazepine-like hypnotic activity (Shinomiya K, et al. (2005). Hypnotic activities of chamomile and passiflora extracts in sleep-disturbed rats. *Biot Pharm Bull*, 28(5): 808-810), have shown moderate effect sizes on total sleep time relative to placebo treatments in subjects with insomnia (Sarris J, et al. (2011). Herbal medicine for depression, anxiety and insomnia: A review of psychopharmacology and clinical evidence. *Eur Neuropsychopharm*, 21: 841-860; Zick S M, et al. (2011). Preliminary examination of the efficacy and safety of a standardized chamomile extract for chronic primary insomnia: A randomized placebo-controlled pilot study. *BMC Complement Altern Med*, 11:78). Other studies have achieved significant impacts on the hastening of sleep onset using *Matricaria ricotta* (Gould L, et al. (1973). Cardiac effect of chamomile tea. *J Clin Pharmacol*, 13: 475-479).

Melatonin is a hormone produced by the pineal gland from the amino acid tryptophan. Production is rhythmic in keeping with an intrinsic cycle of approximately 24 hours in duration, wherein levels are low and increase toward the nighttime (Wyatt J K, et al. (1999). Circadian temperature and melatonin rhythms, sleep, and neurobehavioral function in humans living on a 20-h day. *Am J Physiol*, 277(4 Pt 2): R1151-1163). Melatonin appears to have two distinct effects on the circadian clock: neuronal inhibition and phase-shifting of the sleep cycle (Liu C, et al. (1997). Molecular dissection of two distinct atoms of melatonin on the suprachiasmatic circadian clock. *Neuron*, 19(1): 91-102). Oral administration of supplemental melatonin during the day induces sleepiness and improves night sleep (Dollins A B, et al. (1994). Effect of inducing nocturnal serum melatonin concentrations in daytime on sleep, mood, body temperature, and performance. *Proc Natl Acad Sci USA*, 91(5): 1824-1828).

The existing market of sedative-hypnotics came fully into being in 1971 with flurazepam and the era of benzodiazepines (Mitler, M M. (2000). Nonselective and selective benzodiazepine receptor agonists: where are we today? *Sleep*, 23 (Suppl. 1): S39-S47). It has now expanded to include drugs like zolpidem (Ambien), eszopiclone (Lunesta), ramelteon (Rozerem), zaleplon (Sonata), and doxepine (Silenor), and benzodiazepines like triazolam (Halcion), temazepam (Restoril), and alprazolam (Xanax).

Studies have shown that even the novel classes of non-benzodiazepine hypnotic drugs ("Z-drugs") lead to negative side effects, including physical effects like impaired balance (Allain H, et al. (2003). Effects on postural oscillation and memory functions of a single dose of zolpidem 5 mg, zopiclone 3.75 mg and lormetazepam 1 mg in elderly healthy subjects. A randomized, cross-over, double-blind study versus placebo. *Euro J Clin Pharmacol*, 59(3): 179-188; Frey D J, et al. (2011). Influence of zolpidem and sleep inertia on balance and cognition during nighttime awakening; a randomized placebo-controlled trial. *J Am Geriatr Soc*, 59(1): 73-81) and increased mortality (Kripke D F, et al. (2012). Hypnotics' association with mortality or cancer: a matched cohort study. *BMJ Open*, 2:e000850), as well as cognitive effects like impairment of task performance and severe disruption of memory (Pompeia, S., et al. (2004). Zolpidem and memory: A study using the process-dissociation procedure. *Psychopharmacology*, 174(3): 327-333; Huang, M P., et al. (2010). Effects of eszopiclone and zolpidem on sleep-wake behavior, anxiety-like behavior, and contextual memory in rats. *Behav Brain Res*, 210(1): 54-66; Stranks E K, Crowe S F. (2014). The acute cognitive effects of zopiclone, zolpidem, zaleplon, and eszopiclone: A systematic review and meta-analysis. *J Clin Exp Neuropsyc*, 36(7): 691-700; Allain H, et al. (2003). Effects on postural oscillation and memory functions of a single dose of zolpidem 5 mg, zopiclone 3.75 mg and lormetazepam 1 mg in elderly healthy subjects. A randomized, cross-over, double-blind study versus placebo. *Euro J Clin Pharmacol*, 59(3): 179-188; Frey D J, et al. (2011). Influence of zolpidem and sleep inertia on balance and cognition during nighttime awakening; a randomized placebo-controlled trial. *J Am Geriatr Soc*, 59(1): 73-81.), illusions and hallucinations (Stone J R, Tsuang J. (2008). Dose-related illusions and hallucinations with zaleplon. *Clin Toxicol*, 46: 344-345.) and addiction and dependence in as high as 47% of subjects (de las Cuevas, C. (2003). Benzodiazepines: more "behavioral" addiction than dependence. *Psychopharmacology*, 167(3): 297-303).

Studies have demonstrated not only strong correlations with the above side effects, but also limited effectiveness as a sleep aid. Some studies have shown that there is no potentiation of sleep by stimulation of the GABAA receptor and benzodiazepine binding sites (Mendelson, W B, Martin, J V. (1990). Effects of muscimol and flurazepam on the sleep EEG in the rat. *Life Sci*, 47, PL99-PL101; Lancel, M, et al. (1997). Muscimol and midazolam do not potentiate each other's effects on sleep EEG in the rat. *J. Neurophysiol*, 77: 1624-1629). While stimulation of the benzodiazepine binding site promotes slow-wave sleep in humans, particularly stage II (with spindle enhancement), traditional sleep aids operate at the expense of sleep stages III and IV, and inhibit paradoxical sleep and its eye movements (the deepest stage of sleep, characterized by delta waves—also known as "REM sleep") (Gaillard, J M, et al. (1973). Effects of three benzodiazepines (nitrazepam, flunitrazepam and bromazepam) on sleep of normal subjects, studied with an automatic scoring system. *Pharmakopsychiatrie*, 6: 207-217; Borbely, A A, et al., (1985). Effect of benzodiazepine hypnotics on all-night sleep EEG spectra. *Hum. Neurobiol.*, 4: 189-194; Monti, J M, Altier, H. (1973). Flunitrazepam (Ro 5-4200) and sleep cycle in normal subjects. *Psycho-pharmacologia*, 32: 343-349; Mendelson, W B, Martin, J V, 1990. Effects of muscimol and flurazepam on the sleep EEG in the rat. *Life Sci*, 47: PL99-PL101; Lancel, M, et al., (1996). Role of GABAA receptors in sleep regulation: Differential effects of muscimol and midazolam on sleep in rats. *Neuropsychopharmacology*, 15: 63-74.) In sum, existing sleep aids decrease waking, increase slow-wave sleep, and enhance the intermediate stage between slow-wave sleep and paradoxical sleep, but do so at the expense of paradoxical or REM sleep.

The interruption of this critical stage of sleep by traditional sleep aids is critical, as studies have shown that reduced paradoxical sleep is necessary for learning ability and memory (Fishbein W, Gutwein B M. (1977). Paradoxical sleep and memory storage processes. 19(4): 425-464; Gutwein B M, et al. (1980). Paradoxical sleep and memory: Long-term disruptive effects of anisomycin. *Pharmacol Biochem Behav*, 12(3): 377-384.) and brain development (Mirmiran M, Van Someren, E. (1993). The importance of REM sleep for brain maturation. *J Sleep Res*, 2: 188-192.)

DETAILED DESCRIPTION OF THE INVENTION

In certain embodiments, the present invention comprises a customized bilayer caplet comprised of two layers: immediate release and time release. In contrast to traditional sleep aids, the invention's two unique layers are designed to provide a three (3) phase approach to falling asleep. The immediate release layer is composed of non-habit forming herbal ingredients: one hundred (100.0) mg of L-Theanine, sixty two-and-a-half (62.5) mg of Skullcap Herb (*Scutellaria lateriflora* L.), one hundred (100) mg of Rhodiola (*Rhodiola rosea* L.), and five (5.0) mg of Chamomile Flower (*Matricaria Recutita*). This layer is used in conjunction with a time release layer, containing five (5.0) mg of Melatonin. This time release layer is designed to release not more than (NMT) 50% melatonin after 15 minutes, NMT 75% after 1 hour, and not less than 85% after 6 hours. The use of the immediate release layer catalyzes the pre-calming Phase 1, which promotes calmness, relaxation, and stress relief, whereas the timed release melatonin layer helps to prepare the body and mind for Phase 2, which is the induction of sleep. The extended time release of melatonin then provides a steady dose of melatonin to keep the individual asleep during Phase 3. This unique dosage form allows for the individual to avoid the negative side effects associated with traditional sleep aids, while also retaining the full benefit of all stages of sleep, including the paradoxical or "REM" stage.

Multi-layer tablet dosage forms are capable of achieving unique product performance objectives not otherwise achievable by conventional tablets (Vaithiyalingam, S R, Sayeed, V A. (2010). Critical factors in manufacturing multi-layer tablets—assessing material attributes, process controls, manufacturing process and product performance. *Int. J. Pharm.*, 398: 9-13.). This design feature is characterized by several advantages, including control of the delivery rate of either single (Bogan, 2008) or two different active pharmaceutical ingredient(s) (APIs) (Kulkarni and Bhatia, 2009; Nirmal et al., 2008), the separation of incompatible APIs from one another or controlled release of APIs from one layer through utilization of the functional property of the other layer (i.e., osmotic property) (Vaithiyalingam, S R, Sayeed, V A. (2010). Critical factors in manufacturing multi-layer tablets-assessing material attributes, process controls, manufacturing process and product performance. *Int. J. Pharm.*, 398: 9-13.), modification of the total surface area available for API layer, either by sandwiching with one or two inactive layers in order to achieve swellable/erodible barriers for modified release (Efentakis M, Peponaki C. (2008). Formulation study and evaluation of matrix and three-layer tablet sustained drug delivery systems based on car-pools with isosorbite mononitrate. *AAPS PharmSciTech* 9: 917-923; Phaechamud T. (2008). Variables influencing drug release from layered matrix system comprising hydroxypropyl methylcelluose. *AAPS PharmSciTech* 9: 668-674.), administration of fixed dose combinations of different APIs (LaForce C. et al. (2008) A randomized, double-blind, parallel-group, multicenter, placebo-controlled study of the safety and efficacy of extended-release guaifenesin/pseudoephedrine hydrochloride for symptom relief as an adjunctive therapy to antibiotic treatment of acute respiratory infections. *Postgrad. Med.* 120: 53-59), prolongation of the drug product lifecycle (Vaithiyalingam, S R, Sayeed, V A. (2010). Critical factors in manufacturing multi-layer tablets—assessing material attributes, process controls, manufacturing process and product performance. *Int. J. Pharm.*, 398: 9-13.), fabrication of novel drug delivery systems, such as chewing devices (Maggi et al. (2005). Preparation and evaluation of release characteristics of 3TabGum, a novel chewing device. *Eur. J. Pharm. Sci.* 24: 487-493.), buccal/mucoadhesive delivery systems (Park, C. R., Munday, D. L. (2002). Development and evaluation of a biphasic buccal adhesive tablet for nicotine replacement therapy. *Int. J. Pharm.* 237: 215-226.), and floating tablets for gastro-retentive drug delivery (Sungthongjeen, S., et al. (2008). Design and evaluation of floating multi-layer coated tablets based on gas formation. *Eur. J. Pharm. Biopharm.* 69: 255-263.).

Bilayer tablets present manufacturing and design challenges, including the design of tablets that do not fracture at the interface because of insufficient adhesion (Akseli, I., et al. (2013). Mechanistic characterization of bilayer tablet formulations. *Powder Technol.* 236: 30-36; Kottala, N., et al. (2013). Characterization of interfacial strength of layered powder-compacted solids. *Powder Technol.* 239: 300-307), resulting in delamination during manufacturing, packaging, and storage (Klinzing, G., Zavaliangos, A. (2013). Understanding the effect of environmental history on bilayer tablet interfacial shear strength. *Pharm. Res.* 30: 1300-1310; Kottala, N., et al. (2012). Influence of compaction properties and interfacial topography on the performance of bilayer tablets. *Int. J. Pharm.* 436: 171-178; Kottala, N., et al. (2012). Evaluation of the performance characteristics of bilayer tablets: Part I. Impact of material properties and process parameters on the strength of bilayer tablets. *AAPS PharmSciTech* 13: 1236-1242; Kottala, N., et al. (2012). Evaluation of the performance characteristics of bilayer tablets: Part II. Impact of environmental conditions on the strength of bilayer tablets. *AAPS PharmSciTech* 13: 1190-1196.), as well as other problems, such as binding, sticking, picking, filming, capping, and chipping (Fung K Y, Ng K M. (2009). Product-centered processing and manufacturing: pharmaceutical tablets and capsules. *AIChE. J.*, 49(5): 1193-1215.)

The design and development of solid dosage forms and galenical processes rely on the physicochemical and mechanical properties of the active, excipient components and mixtures thereof (Iyer R M, et al. (2014). The impact of roller compaction and tablet compression on physicomechanical properties of pharmaceutical excipients. *Pharm Dev Technol*, 19)5_: 583-592.) The physical properties are closely linked to final product specifications such as purity, uniformity, dissolution, stability, appearance and mechanical durability (Hlinak A J, Kuriyan K, Morris K R, et al. (2006). Understanding critical material properties for solid dosage form design. *J Pharm Innovation* September/October: 12-17.). While physical properties clearly influence powder flow and compression, the effects of mechanical properties of materials on their behaviour during galenical processing has been demonstrated by instrumented tablet press, compaction simulator and mechanical testing devices (Vachon M G, Chulia D. (1999). The use of energy indices in estimating powder compaction functionality of mixtures in pharmaceutical tableting. *Int J Pharm* 177:183-200.).

In particular, studies have shown that tablet hardness, disintegration time and friability are markedly influenced by tablet hardness and compression force (Kathpalia, H., et al. (2014). Controlled release orally disintegrating tablets: A review. *IJPSR,* 24(1), 35-42.). The hardness, or "break force", of solid tablets serves as an important quality-control specification. An extremely hard tablet could indicate excessive bonding potential between active ingredients and excipients, which can lead to increased disintegration times and prevent proper dissolution of the tablet needed for an accurate dosage, whereas an excessively soft tablet may signify weak bonding and a likelihood of high friability and premature disintegration upon ingestion, as well as fracture, chipping, or breaking throughout the various stages of manufacture, such as coating and packaging. (Chiang E. (2013). Measuring tablet hardness: a primer. *Pharmaceutical Technology*, 37(6): 42.). Additionally, capping and lamination, or the horizontal and vertical breakup of the tablet, are caused by expansion of air entrapped in granulation which cannot escape during compression, and can be improved by reducing compression pressure (Fung K Y, Ng K M. (2009). Product-centered processing and manufacturing: pharmaceutical tablets and capsules. *AIChE. J.,* 49(5): 1193-1215.). Reducing compression pressure can also assist in shortening disintegration time by increasing porosity, as well as in the prevention of capping and lamination (horizontal and vertical breakup of the tablet) caused by the expansion of air entrapped in granulation, which cannot escape during compression. For a weak tablet, bonding force among particles can be increased by increasing the compaction pressure.

In short, the development and production of quality bilayer tablets requires a comprehensive understanding of the product and process in order to achieve accuracy in weight control of each individual layer, de-lamination/layer-separation during manufacturing and storage, and sufficient tablet breaking force and prevention of cross-contamination between the layers (especially for incompatible APIs) (Vaithiyalingam, S R, Sayeed, V A. (2010). Critical factors in manufacturing multi-layer tablets—assessing material attributes, process controls, manufacturing process and product performance. *Int. J. Pharm.*, 398: 9-13.). In this regard, the present invention has harnessed the above information, exploiting the correlation between hardness, disintegration, dissolution, friability, percentage defective and weight variation, and manipulating the various parameters to produce a dosage form with optimum characteristics. The present invention encompasses a unique Bi-Layer Technology, utilizing two separate hardnesses to deliver two separate and distinct formulae in one unit dose, in which there is minimal contact between the two layers for improved release profile and product stability. Caplets are compressed using a double sided tablet press, in which the first tablet layer is partially created using the brown premix, without ejection from the die cavity, followed by a second filling using the light bluish-green premix, and final compression and ejection from the tablet press.

Hardness is a critical parameter for this bilayer tablet. During the development stage, optimum tablet compression parameters are determined by the physical parameters of the tablet (i.e. hardness of $1^{st}$ layer, then total hardness of bilayer), which also affects the time release profile. For this formula, hardness is to be checked by operators in production every 30 minutes, as opposed to other tablet parameters, which are monitored every 90 minutes. For this formulation, two individual premixes are blended, forming the bilayer caplet. During development, the thin light bluish/green (time release) layer required three trials in total to reach optimum blending and tablet properties.

Initially, a small portion of melatonin was being added to the immediate release layer. After performing dissolution testing, it was found that the melatonin was being released too quickly, preventing the immediate release layer ingredients from taking effect prior to the effects of melatonin. The premix blends were modified by relocating all melatonin ingredients to the time release layer. During initial trials, modifications were also made to excipients for cost purposes. These modifications did not alter the properties of the premix.

The challenging layer in terms of development was found to be the thicker brown layer (immediate release), requiring a total of seven trials to reach optimum blending and tablet properties. This layer was much thicker by weight proportion (1000 mg: 300 mg), and every possible effort was made to reduce tablet size and, for aesthetic purposes, to render the layers more proportional.

Hardness is a critical factor when compressing this bilayer tablet. During the $2^{nd}$ production trial, it was determined that a hardness range of 7-13 kp would be the optimum range for this layer of the tablet (target 10 kp). Increasing compression force was studied, producing a tougher tablet resulting in a hardness of 17 and 29 kp, in which splitting of the bilayer tablet was observed at 29 kp. After these trials, it was determined that the target tablet hardness would be 30 kp, with the brown layer compressed at a target of 10 kp. During the $3^{rd}$ production trial, it was observed that anything over 13 kp for the brown layer causes a larger spread or variation between hardness in the tablets tested. Additionally, after mixing, a large amount of powder was observed at the bottom of the blender, prompting modification of the blending sequence for improved mixing in subsequent trials. Throughout the trials, modifications were also made to the ingredients, including microcrystalline cellulose (MCC), dicalcium phosphate (DCP), rhodiola, and silicon dioxide (Syloid) content. These modifications, and the modification of compression pressure to achieve different tablet hardnesses, were capable achieving significant reductions in the tablet's friability and observed chipping of the tablet's edges.

Through alternate testing of each layer, it was found that the light bluish-green layer compressed more optimally than the brown layer. In comparison to the brown layer, the thinner layer was found to have a much higher hardness, and tended to overcome the lower hardness of the brown layer when the tablet was tested as a whole. The optimum hardness specification for the final tablet was found to be 7-10 kp for the immediate release (brown layer) and 27-31 kp for the final hardness of the tablet (See Table 1). The final bilayer caplet is coated, making it easier to swallow, with peppermint oil for odour masking. With these optimum parameters assessed for each layer, the tablet satisfies all of the requisite physical and chemical parameters to deliver the ingredients as intended.

TABLE 1

Melatonin Time Release Profile

| Hardness (kp) | Time (minutes) | Melatonin Released (%) |
| --- | --- | --- |
| 28 | 15 | 20 |
| 28 | 60 | 57 |
| 28 | 360 | 99 |
| 30 | 15 | 18 |
| 30 | 60 | 52 |
| 30 | 360 | 98 |

US Patent Application 20080248106 claims a sleep aid composition comprising the administration of a supplemental composition comprising melatonin, lavender flower extract, and Ferula extract. The composition may be in a layered solid dosage form to provide controlled and sustained release of specific ingredients. While the dosage form is similar, this patent does not proffer the same benefits as those mentioned above.

US Patent Application 20080254121 claims a sleep aid composition comprising a multi-layered solid dosage form for oral administration for a multi-phasic controlled release of Melatonin. This patent does not encompass the use of additional herbal ingredients, as comprised by this invention.

WO Patent Application 2005063297 discloses a melatonin combination therapy comprising a sedative agent and melatonin agent, with a preferred embodiment in which the sedative agent is eszopiclone. The present invention avoids the combination with this class of sedative-hypnotics, which are correlated with the above-mentioned side effects.

US Patent Application 20140171478 claims a sleep aid composition comprising melatonin, a pH lowering agent, and a gel-forming forming polymer, wherein tablet hardness is formulated to release melatonin into the intestines for a sustained time period. However, this patent does not extend beyond the use of melatonin, nor does it make use of the additional, non-habit forming herbal ingredients contemplated by the present invention.

US Patent Application 20140171479 comprises a composition of melatonin dispersed in a polymer matrix, adapted to release an effective amount of melatonin into the subject's intestines. While tablet compression was also monitored in this patent, as above, the patent does not extend beyond the use of melatonin, nor does it make use of the additional, non-habit forming herbal ingredients contemplated by the present invention.

In the following description, for the purposes of explanations, numerous specific details are set forth in order to provide a thorough understanding of the present invention. It will be apparent, however, to one of ordinary skill in the art, that the present invention may be practiced without these specific details.

In certain embodiments, the present invention is directed towards compositions and methods to improve sleep onset, quality, and duration. Advantageously, the use of a solid dosage form, comprised of multiple, distinct layers with distinct properties or sequential arrangement, allows for the manipulation and control of the release of constituents contained within the various layers.

As used herein, the term "immediate release" format is understood to be defined as pertaining to the dissolution and bioavailability profile of an ingested dietary ingredient wherein no additional modifications, be it chemical or physical, have been made to the ingredient with the specific intent to alter the dissolution or bioavailability profile from that of ingredient in a naturally occurring form. It is also understood that immediate release is, literally, immediate release of active ingredients. This is further understood to be a traditional or conventional release format where no slow, delayed, or extended release modifiers are therein incorporated.

As used herein, the term "controlled release" format is understood to be defined as a formulation and/or the physical arrangement of active ingredients and appropriate excipients in a specific format to facilitate a controlled or non-immediate release of active ingredients. The components of a controlled-release format may have been subjected to additional modifications, be it chemical or physical, with the specific intent to alter the dissolution or bioavailability profile from that of ingredient in a naturally occurring form.

As used herein the term "slow release" format is understood to be defined as a controlled release format wherein the release of active ingredients is delayed for a period of time or gradually released over an extended period of time. This is accomplished through the use of specific excipients and may include structural features designed to facilitate controlled-release. It is further understood that a slow-release format releases active ingredients at a rate slower than immediate-release.

An immediate release dosage form may be formulated as a tablet or multiparticulate which may be encapsulated. Other immediate release dosage forms known in the art can be employed. In certain embodiments, the combination of therapeutic agents may be formulated to provide for an increased duration (sustained release) of therapeutic action.

The therapeutic agent Melatonin can also be formulated as a controlled or sustained release oral formulation in any suitable tablet, coated tablet or multiparticulate formulation known to those skilled in the art. The sustained release dosage form may optionally include a sustained released carrier which is incorporated into a matrix along with the active agents, or which is applied as a sustained release coating.

The sustained release dosage form may include the melatonin in controlled or sustained release form and the other therapeutic agents in the sustained release form or in immediate release form. The other therapeutic agents may be incorporated into the sustained release matrix along with the melatonin; incorporated into the coating; incorporated as a separated sustained release layer or immediate release layer; or may be incorporated as a powder, granulation, etc., in a gelatin capsule with the substrates of the present invention. Alternatively, the sustained release dosage form may have the melatonin in the sustained release form and the other therapeutic agents in the sustained release form or immediate release form.

In a preferred embodiment of the present invention, the composition comprises at least two distinct layers being positioned interior to an outer-most coating. The composition comprises therapeutic agents including L-Theanine, Skullcap Herb (*Scutellaria lateriflora* L.), Rhodiola (*Rhodiola rosea* L.), and Chamomile Flower (*Matricaria Recutita*), and Melatonin. The therapeutic agents will be released in a pre-determined manner according to the characteristics of the layer, as set forth below.

In a preferred embodiment, the first layer contains from about 50 mg to 150 mg of the following medicinal ingredients, available for an immediate release having a time period of about less than sixty seconds: L-Theanine, Skullcap Herb (*Scutellaria lateriflora* L.), Rhodiola (*Rhodiola rosea* L.), and Chamomile Flower (*Matricaria Recutita*). The preferred amount of medicinal ingredients in the coating is approximately as follows: 100 mg L-Theanine, 62.5 mg Skullcap Herb (*Scutellaria lateriflora* L.), 100 mg. Rhodiola (*Rhodiola rosea* L.), and 5.0 mg Chamomile Flower (*Matricaria Recutita*).

The solid dosage form comprises a plurality of components sequentially arranged in layers from the outmost to the innermost of said solid dosage form; an outer coating, a first layer, and a second layer. Each of the layers contains a dosage of excipients and a therapeutically effective amount of medicinal ingredients. The density of the first layer and second layer are determined by the excipients and the compression applied during manufacturing to each of the layers. The outer coating as applied to the solid dosage form eases ingestion and masks odor. It begins to dissolve within about 1 minute following administration to a mammal and thus constitutes an immediate release profile. The first layer begins to dissolve within about 60 seconds following administration to a mammal and is completely dissolved within about 2 hours following administration. The second layer begins to dissolve following the dissolution of the first layer at about 2 hours from the point of administration, and is completely dissolved within about 7 hours following administration to a mammal. The interconnection of the dissolution profiles of the components of the present invention in this embodiment form a multi-phasic temporal release profile.

In certain embodiments, the present invention or those similarly envisioned by one of skill in the art may be utilized in methods to promote and maintain a state of sleep in an individual. As such, the present invention may be used in conjunction with other methods known to promote and maintain a state of sleep. Additionally, the present invention may incorporate additional ingredients known to promote and maintain a state of sleep.

In a preferred embodiment of the present invention, melatonin and other medicinal ingredients may be provided in a solid dosage form having specific controlled release characteristics. Advantageously, the composition may be provided in a layered solid dosage form. In such a form, each individual layer will provide unique dissolution characteristics. In this way a controlled release of the composition can be achieved.

In one aspect of this embodiment, each layer contains a homogeneous mixture of ingredients whereby the release of all ingredients is dependent upon the characteristics of each given layer. In an alternative aspect of this embodiment, each layer contains a distinct set of specific ingredients which differ according to the layers such that different specific ingredients are released from the solid dosage form at different times according to a predetermined schedule. In all aspects of this embodiment, a temporally controlled release of ingredients is achieved.

It is herein understood that the immediate release of a therapeutically effective amount of medicinal ingredients from the first layer will promote the onset of a state of sleep. Additionally, it is herein understood that a further release of melatonin, from about 2 hours to about 7 hours, will act to maintain a state of sleep.

The dosage form of the nutritional supplement may be provided in accordance with customary processing techniques for herbal and nutritional supplements in any of the forms mentioned above. Additionally, the nutritional supplement set forth in the example embodiment herein may contain any appropriate number and type of excipients, as is well known in the art.

Although the following examples illustrate the practice of the present invention in its embodiments, the examples should not be construed as limiting the scope of the invention. Other embodiments will be apparent to one of skill in the art from consideration of the specifications.

EXAMPLES

Example 1

A supplementary composition to aid in achieving a full night's sleep in the form of a caplet. The supplementary composition consists of the following:

An outer coating comprising peppermint oil to ease ingestion and mask odour, a first layer comprising from about 50 mg to 150 mg of the following medicinal ingredients, available for an immediate release having a time period of about less than sixty seconds: L-Theanine, Skullcap Herb (*Scutellaria lateriflora* L.), Rhodiola (*Rhodiola rosea* L.), and Chamomile Flower (*Matricaria Recutita*), wherein the preferred amount of medicinal ingredients in the coating is approximately as follows: 100 mg L-Theanine, 62.5 mg Skullcap Herb (*Scutellaria lateriflora* L.), 100 mg. Rhodiola (*Rhodiola rosea* L.), and 5.0 mg Chamomile Flower (*Matricaria Recutita*), and a second layer comprising about 5.0 mg Melatonin, available for a controlled release having a time period of about less than 8 hours.

Example 2

A supplementary composition to aid in achieving a full night's sleep in the form of a caplet. The supplementary composition consists of the following:

A first layer comprising from about 50 mg to 150 mg of the following medicinal ingredients, available for an immediate release having a time period of about less than sixty seconds: L-Theanine, Skullcap Herb (*Scutellaria lateriflora* L.), Rhodiola (*Rhodiola rosea* L.), and Chamomile Flower (*Matricaria Recutita*), wherein the preferred amount of medicinal ingredients in the coating is approximately as follows: 100 mg L-Theanine, 62.5 mg Skullcap Herb (*Scutellaria lateriflora* L.), 100 mg. Rhodiola (*Rhodiola rosea* L.), and 5.0 mg Chamomile Flower (*Matricaria Recutita*), and a second layer comprising about 5.0 mg Melatonin, available for a controlled release having a time period of about less than 8 hours.

Example 3

A supplementary composition to aid in achieving a full night's sleep in the form of a caplet. The supplementary composition consists of the following:

A first layer comprising from about 50 mg to 150 mg of the following medicinal ingredients, available for an immediate release having a time period of about less than sixty seconds: L-Theanine, Skullcap Herb (*Scutellaria lateriflora* L.), Rhodiola (*Rhodiola rosea* L.), and Chamomile Flower (*Matricaria Recutita*), wherein the preferred amount of medicinal ingredients in the coating is approximately as follows: 100 mg L-Theanine, 62.5 mg Skullcap Herb (*Scutellaria lateriflora* L.), 100 mg. Rhodiola (*Rhodiola rosea* L.), and 5.0 mg Chamomile Flower (*Matricaria Recutita*), and a second layer comprising about 5.0 mg Melatonin, available for a slow release having a time period of about less than 8 hours, wherein the release of Melatonin is delayed for a period of time or gradually released over an extended period of time through the use of specific excipients and/or structural features.

In the foregoing specification, the invention has been described with a specific embodiment thereof, however, it will be evident that various modifications and changes may be made thereto without departing from the broader spirit and scope of the invention.

The full disclosure of all publications that are cited are hereby incorporated herein by reference for the teachings for which they are cited.

We claim:

1. A composition for promoting sleep in a human or mammal comprising:
   a. about 100 mg L-Theanine per serving;
   b. about 62.5 mg Skullcap Herb (*Scutellaria lateriflora* L.) per serving;
   c. about 100 mg Rhodiola (*Rhodiola rosea* L.) per serving;
   d. about 5.0 mg Chamomile Flower (*Matricaria Recutita*) per serving; and
   e. about 5.0 mg Melatonin per serving.

2. The composition of claim 1, wherein the composition further comprises a controlled release mechanism.

3. The composition of claim 1, wherein the composition is provided in a solid orally administrable dosage form.

4. The composition of claim 3, wherein the Melatonin is incorporated into a controlled release format.

5. A two layer tablet for promoting sleep in a human or mammal comprising
   a. a first layer in immediate release dosage form comprising
      i. about 100 mg L-Theanine;
      ii. about 62.5 mg Skullcap Herb (*Scutellaria lateriflora* L.);
      iii. about 100 mg Rhodiola (*Rhodiola rosea* L.);
      iv. about 5.0 mg Chamomile Flower (*Matricaria Recutita*); and
   b. a second layer comprising about 5.0 mg melatonin in a slow release form.

* * * * *

UNITED STATES PATENT AND TRADEMARK OFFICE
CERTIFICATE OF CORRECTION

PATENT NO. : 10,568,856 B2  
APPLICATION NO. : 15/755349  
DATED : February 25, 2020  
INVENTOR(S) : John Doherty et al.

Page 1 of 1

It is certified that error appears in the above-identified patent and that said Letters Patent is hereby corrected as shown below:

On the Title Page

Item (72), in Inventors' Names, which reads:  
Inventors: John Doherty, Windosr (CA); Soring Popa, Windor (CA); Dore Miller, Should read:  
John Doherty, Windosr (CA); Sorin Popa, Windor (CA); Dore Miller, Signed and Sealed this  
Twenty-second Day of September, 2020

Andrei Iancu  
*Director of the United States Patent and Trademark Office*